United States Patent
De La Rama et al.

(10) Patent No.: US 8,521,305 B2
(45) Date of Patent: Aug. 27, 2013

(54) PERCUTANEOUS LEAD WITH DISTAL FIXATION

(75) Inventors: Alan De La Rama, Cerritos, CA (US); Peter C. Chen, Irvine, CA (US)

(73) Assignee: St. Jude Medical, Inc., St. Paul, MN (US)

( * ) Notice: Subject to any disclaimer, the term of this patent is extended or adjusted under 35 U.S.C. 154(b) by 162 days.

(21) Appl. No.: 13/099,605

(22) Filed: May 3, 2011

(65) Prior Publication Data

US 2011/0282424 A1   Nov. 17, 2011

Related U.S. Application Data

(60) Provisional application No. 61/333,565, filed on May 11, 2010.

(51) Int. Cl.
*A61N 1/00*   (2006.01)

(52) U.S. Cl.
USPC .......................................... 607/117; 607/126

(58) Field of Classification Search
USPC .................................. 607/115–132
See application file for complete search history.

(56) References Cited

U.S. PATENT DOCUMENTS

| | | | |
|---|---|---|---|
| 4,649,938 A * | 3/1987 | McArthur | 607/127 |
| 5,344,439 A | 9/1994 | Otten | |
| 5,733,322 A | 3/1998 | Starkebaum | |
| 6,763,270 B1 * | 7/2004 | Gomperz et al. | 607/126 |
| 7,047,627 B2 | 5/2006 | Black et al. | |
| 7,069,083 B2 | 6/2006 | Finch et al. | |
| 7,890,174 B2 | 2/2011 | Soltis et al. | |
| 7,899,555 B2 | 3/2011 | Morgan et al. | |
| 2008/0039916 A1 | 2/2008 | Colliou et al. | |
| 2009/0132017 A1 * | 5/2009 | Erickson et al. | 607/117 |

* cited by examiner

*Primary Examiner* — Scott Getzow
(74) *Attorney, Agent, or Firm* — Mattingly & Malur, PC

(57) ABSTRACT

A lead includes an elongated body and an anchor segment disposed between the distal end of the body and electrodes on a distal portion of the body. The anchor segment has lobes which are separated by slits and movable between a collapsed position and an expanded position. A positioning mechanism is disposed inside the hollow interior of the body and at least partially within the anchor segment. The positioning mechanism has a distal positioning portion attached to the distal end of the body and a proximal positioning portion. A control member is connected with the proximal positioning portion to control the positioning mechanism to pull the distal end toward the proximal end so as to move the lobes from the collapsed position to the expanded position and to push the distal end away from the proximal end so as to move the lobes from the expanded to the collapsed position.

20 Claims, 5 Drawing Sheets

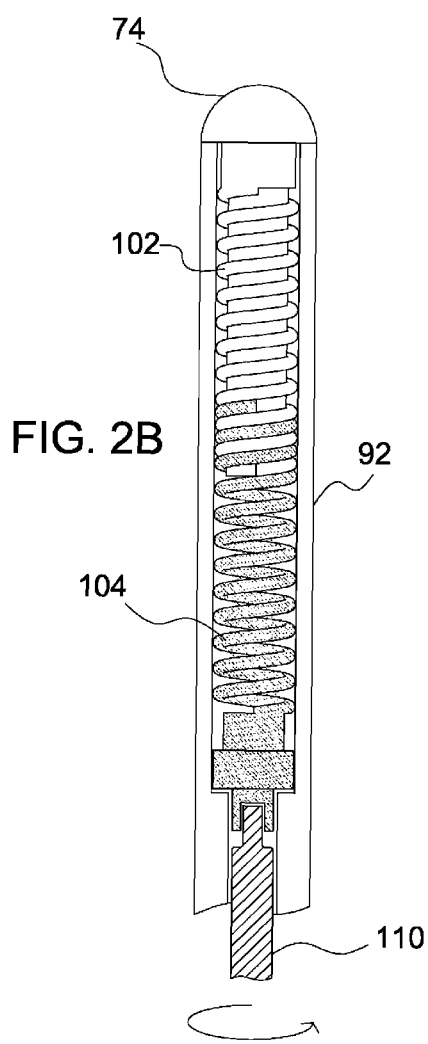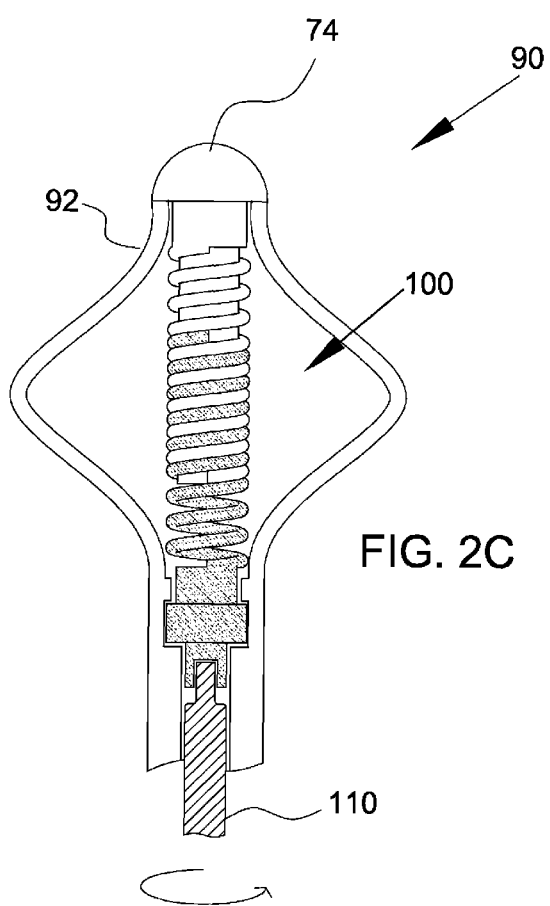

PERCUTANEOUS LEAD WITH DISTAL FIXATION

This application is based on and claims the benefit of U.S. Provisional Patent Application No. 61/333,565, filed May 11, 2010, the entire disclosure of which is incorporated herein by reference.

BACKGROUND OF THE INVENTION

The present invention relates generally to leads and, more specifically, to an anchoring mechanism for a lead such as a neurological epidural lead.

Neurological epidural leads are known. Examples of implantable leads for delivering electrical stimulation to areas such as the epidural regions include U.S. Pat. Nos. 7,047,627 and 7,069,083. The entire disclosures of these patents are incorporated herein by reference. After the lead is implanted at a target location, one of the common complications from spinal cord stimulation (SCS) implants is lead shifting or migration due to movement of the patient or the like. This complication can often result in reduction or loss of paresthesia/pain overlap. In addition, this will present a change in the area of coverage or the appearance of unpleasant sensations during stimulation. An anchoring mechanism can alleviate potential lead migration and the benefits to the patient are numerous which include therapeutic gains and also avoidance of revision surgery with associated risk and expense.

BRIEF SUMMARY OF THE INVENTION

Exemplary embodiments of the invention provide apparatus and methods for anchoring a percutaneous lead inside patient's body, such as a neurological epidural lead in an epidural space. The anchoring mechanism of the present invention can be used to anchor epidural leads or other kinds of percutaneous leads in the body of a patient.

In accordance with an aspect of the present invention, a lead comprises: an elongated body having a distal end, a proximal end, and a hollow interior extending longitudinally therein; a plurality of electrodes on a distal portion of the elongated body adjacent the distal end, the plurality of electrodes being spaced from the distal end of the elongated body and from each other by electrically nonconductive segments, wherein the elongated body includes an anchor segment disposed between the distal end and a first electrode of the plurality of electrodes which is closest to the distal end, the anchor segment having a plurality of lobes which are separated from each other by slits and which are movable between a collapsed position and an expanded position, the first electrode being spaced from the distal end by a maximum distance in the collapsed position, the first electrode being spaced from the distal end by a reduced distance smaller than the maximum distance in the expanded position in which the lobes expand outwardly relative to a longitudinal axis of the elongated body; a positioning mechanism disposed inside the hollow interior of the elongated body and at least partially within the anchor segment, the positioning mechanism having a distal positioning portion attached to the distal end of the elongated body and a proximal positioning portion; and a control member connected with the proximal positioning portion of the positioning mechanism and to control the positioning mechanism to pull the distal end in a proximal direction toward the proximal end so as to move the lobes of the anchor segment from the collapsed position to the expanded position and to push the distal end in a distal direction away from the proximal end so as to move the lobes of the anchor segment from the expanded position to the collapsed position.

In some embodiments, the positioning mechanism comprises an internal lumen tubing disposed inside the hollow interior of the elongated body and movable relative to the elongated body, the internal lumen tubing having a distal tubing portion which is the distal positioning portion attached to the distal end of the elongated body and a proximal tubing portion which is the proximal positioning portion connected with the control member.

In specific embodiments, the positioning mechanism comprises a first mating member which includes the distal positioning portion attached to the distal end of the elongated body and a second mating member which includes the proximal positioning portion, the proximal positioning portion being attached to the elongated body at a position proximal of the anchor segment, the first mating member and the second mating member being in frictional coupling with one another. The frictional coupling is adjustable to move the second mating member relative to the first mating member to pull the distal end in the proximal direction toward the proximal end so as to move the lobes of the anchor segment from the collapsed position to the expanded position and to push the distal end in the distal direction away from the proximal end so as to move the lobes of the anchor segment from the expanded position to the collapsed position. The frictional coupling comprises one of a threaded coupling between threads of the first mating member and threads of the second mating member or a coiled coupling between coils of the first mating member and coils of the second mating member. The frictional coupling is adjustable by rotating the second mating member with respect to the first mating member. The control member comprises a stylet inserted from the proximal end of the elongated body into the hollow interior to engage the second mating member and rotate the second mating member with respect to the first mating member.

In some embodiments, the lobes in the anchor segment are separated by one or more of longitudinal slits or helical slits. The anchor segment has a diameter D in the collapsed position and has at least five lobes, each lobe has a width W, and W is smaller than about $\pi D/10$. The anchor segment has at least ten lobes and W is smaller than about $\pi D/20$.

In accordance with another aspect of the invention, a lead comprises: an elongated body having a distal end, a proximal end, and a hollow interior extending longitudinally therein; a plurality of electrodes on a distal portion of the elongated body adjacent the distal end, the plurality of electrodes being spaced from the distal end of the elongated body and from each other by electrically nonconductive segments; and an internal lumen tubing disposed inside the hollow interior of the elongated body and being attached to the distal end. The elongated body includes an anchor segment disposed between the distal end and a first electrode of the plurality of electrodes which is closest to the distal end, the anchor segment having a plurality of lobes which are separated from each other by slits and which are movable between a collapsed position and an expanded position, the first electrode being spaced from the distal end by a maximum distance in the collapsed position, the first electrode being spaced from the distal end by a reduced distance smaller than the maximum distance in the expanded position in which the lobes expand outwardly relative to a longitudinal axis of the elongated body. The internal lumen tubing is movable relative to the elongated body to pull the distal end in a proximal direction toward the proximal end so as to move the lobes of the anchor segment from the collapsed position to the expanded position and to push the distal end in a distal direction away from the proximal end so as to move the lobes of the anchor segment from the expanded position to the collapsed position. The anchor segment has a diameter D in the collapsed position and has at least five lobes, each lobe has a width W, and W is smaller than about πD/10.

In some embodiments, the lead further comprises a control member attached to the internal lumen tubing at a proximal portion of the elongated body near the proximal end, the control member being slidable relative to the elongated body to move the internal lumen tubing in the proximal direction and in the distal direction. The control member includes a plurality of O-rings in slidable, frictional contact with the elongated body. The elongated body includes a pair of travel stops on opposite sides of the control member to limit travel of the control member relative to the elongated body between the collapsed position of the lobes and the expanded position of the lobes. An elongated body line support tube has a distal support end and a proximal support end and is slidably disposed between the elongated body and the internal lumen tubing, the distal support end being attached to the elongated body at a location proximal of the anchor segment, the proximal support end being disposed in close proximity of the control member without interfering with movement of the control member and the internal lumen tubing.

In accordance with another aspect of this invention, a lead comprises: an elongated body having a distal end, a proximal end, and a hollow interior extending longitudinally therein; a plurality of electrodes on a distal portion of the elongated body adjacent the distal end, the plurality of electrodes being spaced from the distal end of the elongated body and from each other by electrically nonconductive segments, wherein the elongated body includes an anchor segment disposed between the distal end and a first electrode of the plurality of electrodes which is closest to the distal end, the anchor segment having a plurality of lobes which are separated from each other by slits and which are movable between a collapsed position and an expanded position, the first electrode being spaced from the distal end by a maximum distance in the collapsed position, the first electrode being spaced from the distal end by a reduced distance smaller than the maximum distance in the expanded position in which the lobes expand outwardly relative to a longitudinal axis of the elongated body; and a positioning mechanism disposed inside the hollow interior of the elongated body and at least partially within the anchor segment, the positioning mechanism having a first mating member attached to the distal end of the elongated body and a second mating member attached to the elongated body at a position proximal of the anchor segment, the first mating member and the second mating member being in frictional coupling with one another. The frictional coupling is adjustable to move the second mating member relative to the first mating member to pull the distal end in a proximal direction toward the proximal end so as to move the lobes of the anchor segment from the collapsed position to the expanded position and to push the distal end in a distal direction away from the proximal end so as to move the lobes of the anchor segment from the expanded position to the collapsed position.

In some embodiments, the frictional coupling comprises one of a threaded coupling between threads of the first mating member and threads of the second mating member or a coiled coupling between coils of the first mating member and coils of the second mating member. The frictional coupling is adjustable by rotating the second mating member with respect to the first mating member. The lead further comprises a stylet inserted from the proximal end of the elongated body into the hollow interior to engage the second mating member and rotate the second mating member with respect to the first mating member. A proximal portion of the stylet has markings to indicate a first rotational position relative to the elongated body which corresponds to the collapsed position of the lobes and a second rotational position relative to the elongated body which corresponds to the expanded position of the lobes.

These and other features and advantages of the present invention will become apparent to those of ordinary skill in the art in view of the following detailed description of the specific embodiments.

BRIEF DESCRIPTION OF THE DRAWINGS

FIG. 2B is an elevational view of a positioning mechanism of the lead of FIG. 2A illustrating an anchor segment in a collapsed position.

FIG. 2C is an elevational view of the positioning mechanism of FIG. 2B illustrating the anchor segment in an expanded position.

DETAILED DESCRIPTION OF THE INVENTION

Figure 1A:
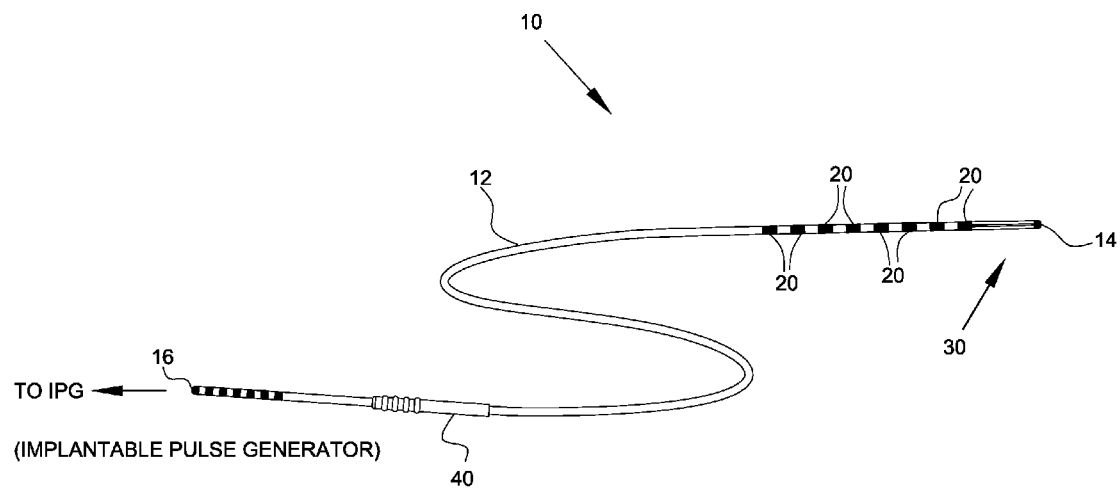
FIG. 1A is a perspective view of a lead with an anchoring mechanism according to an embodiment of the present invention.

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment," "this embodiment," or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Exemplary embodiments of the invention, as will be described in greater detail below, provide apparatuses and methods for anchoring a percutaneous lead such as a neurological epidural lead.

FIG. 1A is a perspective view of a lead with an anchoring mechanism according to an embodiment of the present invention. The lead 10 includes an elongated body 12 having a distal end 14, a proximal end 16, and a hollow interior extending longitudinally therein. A plurality of electrodes 20 are provided on a distal portion of the elongated body 12 adjacent the distal end 14. The plurality of electrodes 20 are spaced from the distal end 14 of the elongated body 12 and from each other by electrically nonconductive segments. An internal lumen tubing 24 is disposed inside the hollow interior of the elongated body 12 and is attached to the elongated body 12 at or near the distal end 14.

Figure 1B:
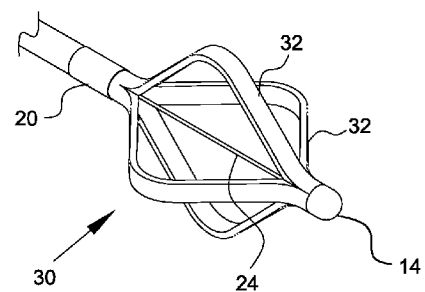
FIG. 1B is a perspective view of an anchor segment of the lead of FIG. 1A.
Figure 1C:
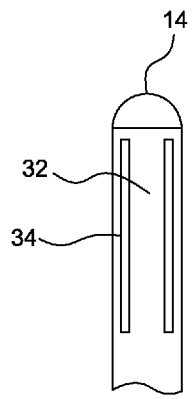
FIG. 1C is an elevational view of the anchor segment of FIG. 1B illustrating longitudinal slits.
Figure 1D:
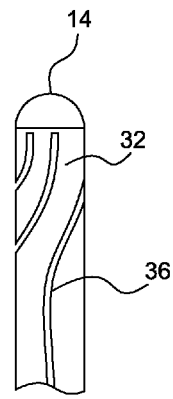
FIG. 1D is an elevational view of the anchor segment of FIG. 1B illustrating helical slits.

The elongated body 12 includes an anchor segment 30 disposed between the distal end 14 and a first electrode 20 of the plurality of electrodes which is closest to the distal end 14. FIG. 1B is a perspective view of the anchor segment 30. The anchor segment 30 has a plurality of lobes 32 which are separated from each other by slits and which are movable between a collapsed/undeployed position and an expanded/deployed position. The first electrode 20 is spaced from the distal end 14 by a maximum distance in the collapsed position, and is spaced from the distal end 14 by a reduced distance smaller than the maximum distance in the expanded position in which the lobes 32 expand outwardly relative to a longitudinal axis of the elongated body 12. Typically, the anchor segment 30 has at least two lobes 32. The lobes 32 are separated, for example, by longitudinal slits 34 (FIG. 1C) or helical slits 36 (FIG. 1D).

The internal lumen tubing 24 is movable relative to the elongated body 12 to pull the distal end 14 in a proximal direction toward the proximal end 16 so as to move the lobes 32 of the anchor segment 30 from the collapsed position to the expanded position and to push the distal end 14 in a distal direction away from the proximal end 16 so as to move the lobes 32 of the anchor segment 30 from the expanded position to the collapsed position. The internal lumen tubing 24 is configured to receive a stylet which can be used to introduce the lead 10 into the patient's body and position the lead 10 at the desired location. The use of a stylet is known in the art. An example is provided in U.S. Pat. No. 7,069,083. For a neurological epidural lead, the lead 10 can be introduced percutaneously. An example is described in U.S. Pat. No. 7,069,083. After the lead is positioned, the stylet is removed and the internal lumen tubing 24 is used as an actuation line to manipulate the anchor segment 30.

Figure 1E:
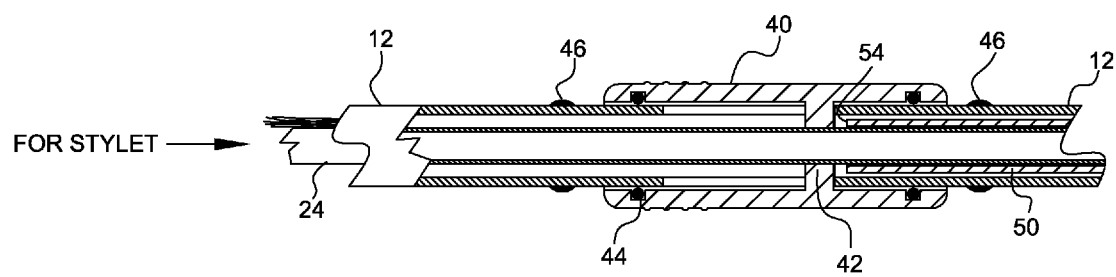
FIG. 1E is a partial sectional view illustrating a control member of the lead of FIG. 1A.

FIG. 1E is a partial sectional view illustrating a control member 40 of the lead of FIG. 1A. The control member 40 is attached to the internal lumen tubing 24 at a proximal portion of the elongated body 12 near the proximal end 16. The connection or attachment 42 between the control member 40 and the internal lumen tubing 24 can be made through one or more longitudinal cuts in the elongated body 12. The control member 40 is slidable relative to the elongated body 12 to move the internal lumen tubing 24 in the proximal direction and in the distal direction. The control member 40 includes a plurality of O-rings 44 in slidable, frictional contact with the elongated body 12. FIG. 1E shows two O-rings 44 near opposite ends of the control member 40. The O-rings 44 also serve as sealing members. The elongated body 12 includes a pair of travel stops 46 on opposite sides of the control member 40 to limit travel of the control member 40 relative to the elongated body 12 between the collapsed position of the lobes 32 and the expanded position of the lobes 32.

An elongated body line support tube 50 has a distal support end (not shown) and a proximal support end 54 and is slidably disposed between the elongated body 12 and the internal lumen tubing 24. The distal support end is attached to the elongated body 12 at a location proximal of the anchor segment 30. The proximal support end 54 is disposed in close proximity of the control member 40 without interfering with movement of the control member 40 and the internal lumen tubing 24. The support tube 50 provides additional structural support or rigidity to the elongated body 12 so that when the internal lumen tubing 24 is pulled in the proximal direction, it causes the lobes 32 of the anchor segment 30 to move to the expanded position and does not cause the elongated body 12 to simply bend without deploying the lobes 32. The elongated body line support tube 50 may be made of a material same or similar to that of the elongated body 12.

Figure 2A:
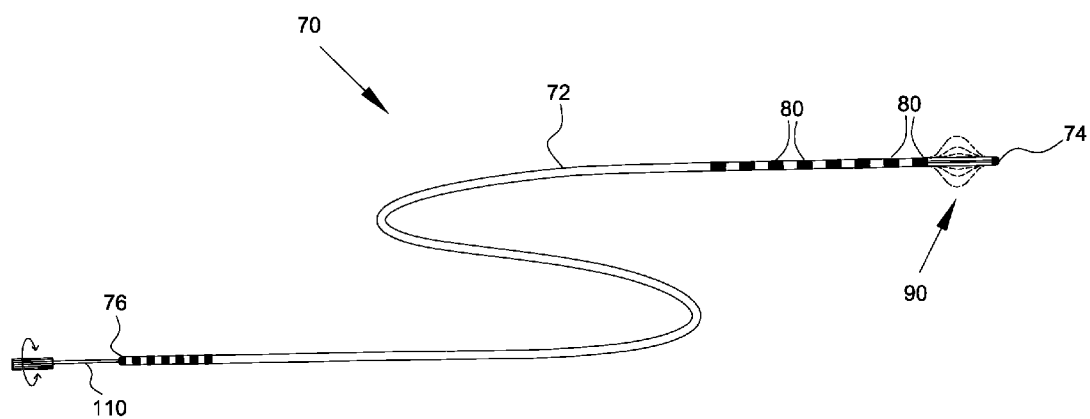
FIG. 2A is a perspective view of a lead with an anchoring mechanism according to another embodiment of the present invention.

FIG. 2A is a perspective view of a lead with an anchoring mechanism according to another embodiment of the present invention. The lead 70 includes an elongated body 72 having a distal end 74, a proximal end 76, and a hollow interior extending longitudinally therein. A plurality of electrodes 80 are provided on a distal portion of the elongated body 72 adjacent the distal end 74. The plurality of electrodes 80 are spaced from the distal end 74 of the elongated body 72 and from each other by electrically nonconductive segments. The elongated body 72 includes an anchor segment 90 having lobes 92 similar to the anchor segment 30 of FIG. 1B. The lobes 92 are separated from each other by slits (the lobes 92 are separated for example by longitudinal slits 34 or helical slits 36 similar to the previous embodiment) and are movable between a collapsed position and an expanded position.

FIG. 2B is an elevational view of a positioning mechanism 100 of the lead 70 of FIG. 2A illustrating an anchor segment in a collapsed position. FIG. 2C shows the positioning mechanism 100 in an expanded position. The positioning mechanism 100 is disposed inside the hollow interior of the elongated body 72 and at least partially within the anchor segment 90. The positioning mechanism 100 has a first mating member 102 attached to the distal end 74 of the elongated body 72 and a second mating member 104 attached to the elongated body 72 at a position proximal of the anchor segment 90. The first mating member 102 and the second mating member 104 are in frictional coupling with one another. The frictional coupling is adjustable to move the second mating member 104 relative to the first mating member 102 to pull the distal end 74 in a proximal direction toward the proximal end 76 so as to move the lobes 92 of the anchor segment 90 from the collapsed position to the expanded position and to push the distal end 74 in a distal direction away from the first electrode 20 which is closest to the distal end 14, so as to move the lobes 92 of the anchor segment 90 from the expanded position to the collapsed position. The frictional coupling comprises one of a threaded coupling between threads of the first mating member 102 and threads of the second mating member 104 or a coiled coupling between coils of the first mating member 102 and coils of the second mating member 104. The frictional coupling is adjustable by rotating the second mating member 104 with respect to the first mating member 102.

Figure 2D:
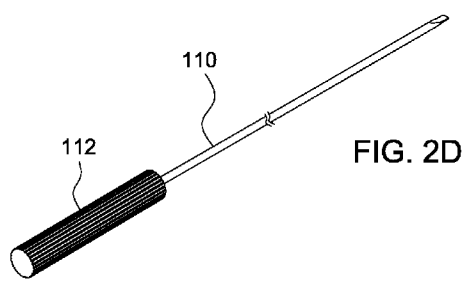
FIG. 2D is a perspective view of a stylet as a control member of the lead of FIG. 2A.

FIG. 2D is a perspective view of a stylet as a control member of the lead of FIG. 2A. The stylet 110 is inserted from the proximal end 76 of the elongated body 72 into the hollow interior to engage the second mating member 104 and rotate the second mating member 104 with respect to the first mating member 102 to move the lobes 92 of the anchor segment 90. The engagement may be similar to that of a screw driver head having a flat head, a Phillips head or a star head. In some embodiments, a proximal portion of the stylet 110 has markings (e.g., on the handle 112) to indicate a first rotational position relative to the elongated body 72 which corresponds to the collapsed position of the lobes 92 and a second rotational position relative to the elongated body 72 which corresponds to the expanded position of the lobes 92. In this way, the operator can make the appropriate rotational adjustments easily based on the markings.

The electrodes on the lead can be used to provide neurological stimulation or the like. The lobes of the anchor segment in the expanded position press against the surrounding biological material (e.g., spinal dura and spinal canal wall for an epidural space) to secure or anchor the lead in place.

Figure 3A:
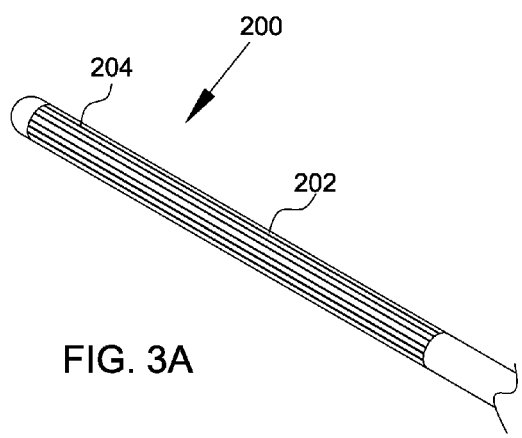
FIG. 3A is a perspective view of the anchoring mechanism in the collapsed position.
Figure 3B:
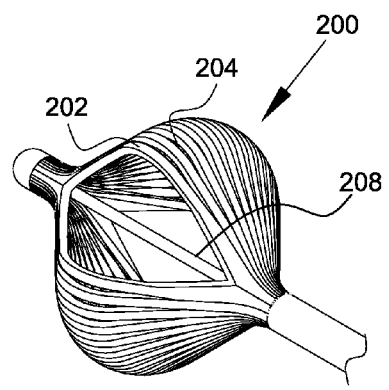
FIG. 3B is a perspective view of the anchoring mechanism of FIG. 3A in the expanded position with self-adjusting fixation.
Figure 3C:
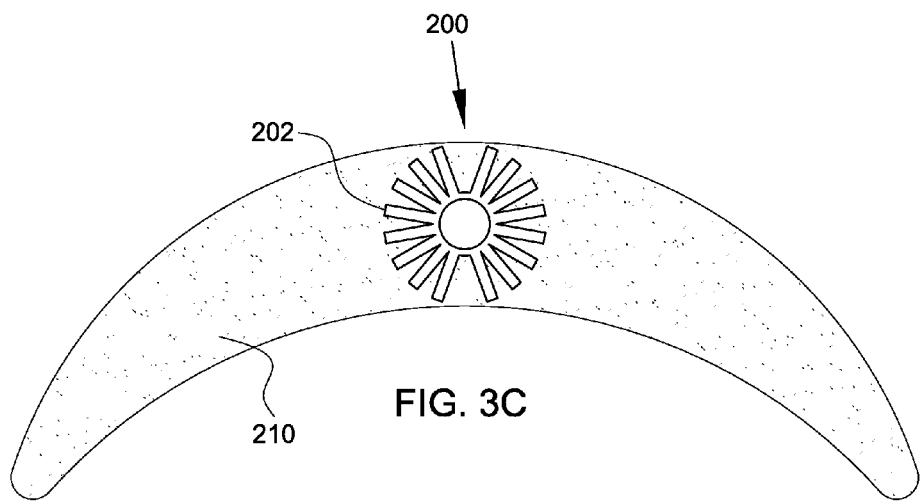
FIG. 3C is a plan view of the anchoring mechanism of FIG. 3B in the expanded position with self-adjusting fixation in an epidural space.

FIG. 3A is a perspective view of the anchoring mechanism 200 in the collapsed position. The anchoring mechanism 200 is similar to the anchor segment 30, 90 of FIGS. 1 and 2, and includes lobes/leaves 202 separated by cuts/slits 204. The lobes 202 can be made of various materials such as nitinol. In general, the number of lobes 202 can vary. The number of lobes 202 determines the circumferential/lateral dimension or width of the lobes 202. In some instances, the anchoring mechanism 202 is disposed within a constrained space such as an epidural space. The ability of the anchoring mechanism 200 to provide self-adjusting fixation is desirable and may be critical. FIG. 3B is a perspective view of the anchoring mechanism 200 in the expanded position with self-adjusting fixation. A positioning mechanism 208 is used to move the anchoring mechanism 200 between the collapsed position and the expanded position. FIG. 3C is a plan view of the anchoring mechanism 200 in the expanded position with self-adjusting fixation in an epidural space 210. The lobes 202 have sufficiently small widths (i.e., sufficiently compliant structurally) to self adjust in the epidural space 210 by shifting the circumferential positions of the lobes 202 from locations with limited space to locations with adequate space to accommodate the expansion of the lobes 202 radially outwardly. As a result, the anchoring mechanism 200 can be fully deployed with self-adjusting repositioning to maximize anchoring. Furthermore, it is desirable for the anchoring mechanism 200 to self adjust the spreading of the lobes 202 in the expanded position so as to avoid impinging on nerves in the vicinity of the epidural space 210. In specific embodiments, the anchoring mechanism or anchor segment 200 has a diameter D in the collapsed/undeployed position and each lobe 202 has a lateral width W, and W is smaller than about $\pi D/4$. For self-adjust anchoring in the epidural space 210 or other tight spaces, it is critical that the width be much smaller and the number of lobes higher, namely, at least five lobes at a width W of smaller than about $\pi D/10$, and more preferably at least ten lobes at a width W of small than about $\pi D/20$. If the width of a lobe is not constant, W can be the maximum width of the lobe. The thickness of the lobe 202 is smaller than the width, and is typically an order of magnitude smaller than the width.

In the description, numerous details are set forth for purposes of explanation in order to provide a thorough understanding of the present invention. However, it will be apparent to one skilled in the art that not all of these specific details are required in order to practice the present invention. Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. A lead comprising:
   an elongated body having a distal end, a proximal end, and a hollow interior extending longitudinally therein;
   a plurality of electrodes on a distal portion of the elongated body adjacent the distal end, the plurality of electrodes being spaced from the distal end of the elongated body and from each other by electrically nonconductive segments, wherein the elongated body includes an anchor segment disposed between the distal end and a first electrode of the plurality of electrodes which is closest to the distal end, the anchor segment having a plurality of lobes which are separated from each other by slits and which are movable between a collapsed position and an expanded position, the first electrode being spaced from the distal end by a maximum distance in the collapsed position, the first electrode being spaced from the distal end by a reduced distance smaller than the maximum distance in the expanded position in which the lobes expand outwardly relative to a longitudinal axis of the elongated body;
   a positioning mechanism disposed inside the hollow interior of the elongated body and at least partially within the anchor segment, the positioning mechanism having a distal positioning portion attached to the distal end of the elongated body and a proximal positioning portion which is movable relative to the distal positioning portion; and
   a control member connected with the proximal positioning portion of the positioning mechanism and to move the proximal positioning portion relative to the distal positioning portion so as to control the positioning mechanism to pull the distal end in a proximal direction toward the proximal end so as to move the lobes of the anchor segment from the collapsed position to the expanded position and to push the distal end in a distal direction away from the proximal end so as to move the lobes of the anchor segment from the expanded position to the collapsed position.

2. The lead of claim 1,
   wherein the positioning mechanism comprises a first mating member which includes the distal positioning portion attached to the distal end of the elongated body and a second mating member which includes the proximal positioning portion, the proximal positioning portion being attached to the elongated body at a position proximal of the anchor segment, the first mating member and the second mating member being in frictional coupling with one another; and wherein the frictional coupling is adjustable to move the second mating member relative to the first mating member to pull the distal end in the proximal direction toward the proximal end so as to move the lobes of the anchor segment from the collapsed position to the expanded position and to push the distal end in the distal direction away from the proximal end so as to move the lobes of the anchor segment from the expanded position to the collapsed position.

3. The lead of claim 2, wherein the frictional coupling comprises one of a threaded coupling between threads of the first mating member and threads of the second mating member or a coiled coupling between coils of the first mating member and coils of the second mating member.

4. The lead of claim 3, wherein the frictional coupling is adjustable by rotating the second mating member with respect to the first mating member; and wherein the control member comprises a stylet inserted from the proximal end of the elongated body into the hollow interior to engage the second mating member and rotate the second mating member with respect to the first mating member.

5. The lead of claim 1, wherein the lobes in the anchor segment are separated by one or more of longitudinal slits or helical slits.

6. The lead of claim 1, wherein the anchor segment has a diameter D in the collapsed position and has at least five lobes, each lobe has a width W, and W is smaller than about $\pi D/10$.

7. The lead of claim 6, wherein the each lobe has a thickness which is an order of magnitude smaller than the width.

8. The lead of claim 6, wherein the anchor segment has at least ten lobes and W is smaller than about $\pi D/20$.

9. A lead comprising:

an elongated body having a distal end, a proximal end, and a hollow interior extending longitudinally therein;

a plurality of electrodes on a distal portion of the elongated body adjacent the distal end, the plurality of electrodes being spaced from the distal end of the elongated body and from each other by electrically nonconductive segments; and an internal lumen tubing disposed inside the hollow interior of the elongated body and being attached to the distal end;

wherein the elongated body includes an anchor segment disposed between the distal end and a first electrode of the plurality of electrodes which is closest to the distal end, the anchor segment having a plurality of lobes which are separated from each other by slits and which are movable between a collapsed position and an expanded position, the first electrode being spaced from the distal end by a maximum distance in the collapsed position, the first electrode being spaced from the distal end by a reduced distance smaller than the maximum distance in the expanded position in which the lobes expand outwardly relative to a longitudinal axis of the elongated body;

wherein the internal lumen tubing is movable relative to the elongated body to pull the distal end in a proximal direction toward the proximal end so as to move the lobes of the anchor segment from the collapsed position to the expanded position and to push the distal end in a distal direction away from the proximal end so as to move the lobes of the anchor segment from the expanded position to the collapsed position; and wherein the anchor segment has a diameter D in the collapsed position and has at least five lobes, each lobe has a width W, and W is smaller than about $\pi D/10$.

10. The lead of claim 9, further comprising:

a control member attached to the internal lumen tubing at a proximal portion of the elongated body near the proximal end, the control member being slidable relative to the elongated body to move the internal lumen tubing in the proximal direction and in the distal direction.

11. The lead of claim 10, wherein the control member includes a plurality of O-rings in slidable, frictional contact with the elongated body.

12. The lead of claim 10, wherein the elongated body includes a pair of travel stops on opposite sides of the control member to limit travel of the control member relative to the elongated body between the collapsed position of the lobes and the expanded position of the lobes.

13. The lead of claim 10, further comprising:

an elongated body line support tube having a distal support end and a proximal support end and being slidably disposed between the elongated body and the internal lumen tubing, the distal support end being attached to the elongated body at a location proximal of the anchor segment, the proximal support end being disposed in close proximity of the control member without interfering with movement of the control member and the internal lumen tubing.

14. The lead of claim 9, wherein the lobes in the anchor segment are separated by one or more of longitudinal slits or helical slits.

15. A lead comprising:

an elongated body having a distal end, a proximal end, and a hollow interior extending longitudinally therein;

a plurality of electrodes on a distal portion of the elongated body adjacent the distal end, the plurality of electrodes being spaced from the distal end of the elongated body and from each other by electrically nonconductive segments, wherein the elongated body includes an anchor segment disposed between the distal end and a first electrode of the plurality of electrodes which is closest to the distal end, the anchor segment having a plurality of lobes which are separated from each other by slits and which are movable between a collapsed position and an expanded position, the first electrode being spaced from the distal end by a maximum distance in the collapsed position, the first electrode being spaced from the distal end by a reduced distance smaller than the maximum distance in the expanded position in which the lobes expand outwardly relative to a longitudinal axis of the elongated body;

a positioning mechanism disposed inside the hollow interior of the elongated body and at least partially within the anchor segment, the positioning mechanism having a first mating member attached to the distal end of the elongated body and a second mating member attached to the elongated body at a position proximal of the anchor segment, the first mating member and the second mating member being in frictional coupling with one another, wherein the frictional coupling is adjustable to move the second mating member relative to the first mating member; and a control member connected with the second mating member to move the second mating member relative to the first mating member to pull the distal end in a proximal direction toward the proximal end so as to move the lobes of the anchor segment from the collapsed position to the expanded position and to push the distal end in a distal direction away from the proximal end so as to move the lobes of the anchor segment from the expanded position to the collapsed position.

16. The lead of claim 15,
wherein the frictional coupling comprises one of a threaded coupling between threads of the first mating member and threads of the second mating member or a coiled coupling between coils of the first mating member and coils of the second mating member.

17. The lead of claim 16,
wherein the frictional coupling is adjustable by rotating the second mating member with respect to the first mating member.

18. The lead of claim 17,
wherein the control member comprises a stylet inserted from the proximal end of the elongated body into the hollow interior to engage the second mating member and rotate the second mating member with respect to the first mating member.

19. The lead of claim 18,
wherein a proximal portion of the stylet has markings to indicate a first rotational position relative to the elongated body which corresponds to the collapsed position of the lobes and a second rotational position relative to the elongated body which corresponds to the expanded position of the lobes.

20. The lead of claim 15,
wherein the anchor segment has a diameter D in the collapsed position and has at least five lobes, each lobe has a width W, and W is smaller than about $\pi D/10$.

\* \* \* \* \*